United States Patent [19]
DeSantis et al.

[11] Patent Number: 5,565,492
[45] Date of Patent: Oct. 15, 1996

[54] PROSTAGLANDIN COMBINATIONS IN GLAUCOMA THERAPY

[75] Inventors: Louis M. DeSantis, Fort Worth; Verney L. Sallee, Burleson, both of Tex.

[73] Assignee: Alcon Laboratories, Inc., Fort Worth, Tex.

[21] Appl. No.: 348,509

[22] Filed: Dec. 1, 1994

Related U.S. Application Data

[63] Continuation of Ser. No. 993,586, Dec. 21, 1992, abandoned, which is a continuation-in-part of Ser. No. 832,662, Feb. 4, 1992, Pat. No. 5,173,507, which is a continuation of Ser. No. 686,101, Apr. 16, 1991, abandoned, which is a continuation-in-part of Ser. No. 422,925, Oct. 17, 1989, abandoned, which is a continuation of Ser. No. 220,204, Jul. 18, 1988, abandoned.

[51] Int. Cl.⁶ .................... A61K 31/215; A61K 31/19; A61K 31/557
[52] U.S. Cl. .................... 514/530; 514/573; 514/913
[58] Field of Search .................... 514/530, 573, 514/912, 913, 922

[56] References Cited

U.S. PATENT DOCUMENTS

| | | | |
|---|---|---|---|
| 4,029,681 | 6/1977 | Smith | 260/408 |
| 4,288,616 | 9/1981 | Sih | 562/503 |
| 4,599,353 | 7/1986 | Bito | 514/530 |
| 5,173,507 | 12/1992 | DeSantis et al. | 514/530 |

FOREIGN PATENT DOCUMENTS

| | | |
|---|---|---|
| 330511A2 | 6/1989 | European Pat. Off. . |
| 0342003A1 | 11/1989 | European Pat. Off. . |
| 364417A1 | 4/1990 | European Pat. Off. . |
| 435682A2 | 7/1991 | European Pat. Off. . |
| 0458587A1 | 11/1991 | European Pat. Off. . |
| 2223365 | 12/1972 | Germany . |
| 9002553 | 3/1990 | WIPO . |

OTHER PUBLICATIONS

The Merck Index, 10th Edition (1983) pp. 1134–1135.
Osol, A., et al. "Remington's Pharmaceutical Sciences", published 1980 by Mack Publishing Co. (PA.), see p. 431.

*Primary Examiner*—Raymond Henley, III
*Attorney, Agent, or Firm*—James A. Arno; Barry L. Copeland

[57] ABSTRACT

Disclosed is the use of combinations of F and E series prostaglandins and their respective derivatives and analogues, as well as pharmaceutically acceptable salts and esters thereof in the treatment of glaucoma and ocular hypertension. Also disclosed are ophthalmic, pharmaceutical compositions comprising said combinations.

18 Claims, No Drawings

PROSTAGLANDIN COMBINATIONS IN GLAUCOMA THERAPY

CROSS-REFERENCE TO RELATED APPLICATIONS

This application is a continuation of U.S. patent application Ser. No. 07/993,586, filed Dec. 21, 1992, now abandoned, which is a continuation-in-part of U.S. patent application Ser. No. 07/832,662 filed Feb. 4, 1992, now U.S. Pat. No. 5,173,507, which is a continuation of U.S. patent application Ser. No. 07/686,101 filed Apr. 16, 1991, now abandoned, which is a continuation-in-part of U.S. patent application Ser. No. 07/422,925 filed Oct. 17, 1989, now abandoned, which is a continuation of U.S. patent application Ser. No. 07/220,204 filed Jul. 18, 1988, now abandoned.

BACKGROUND OF THE INVENTION

This invention relates to the use of combinations of prostaglandins of the F and E series and their derivatives and analogues for the treatment of glaucoma and ocular hypertension. As used herein, the terms "prostaglandin" and "PG" shall refer to prostaglandins and derivatives and analogues thereof, except as otherwise indicated by context.

The structures of the naturally-occurring prostaglandins of the F and E series, of which the prostaglandins of the present invention are derivatives and/or analogues, are shown below:

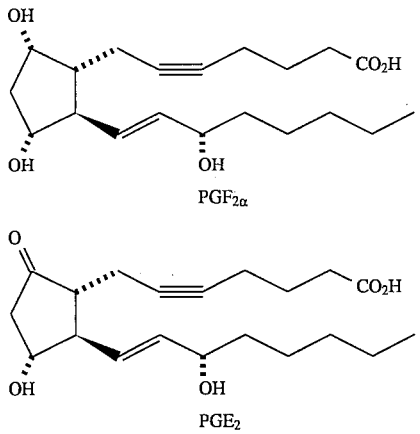

Naturally-occurring prostaglandins are known to lower intraocular pressure (IOP) after topical ocular instillation, but can cause an inflammatory response (hyperemia). Many synthetic prostaglandins have been observed to lower intraocular pressure, but most such compounds also produce the described inflammatory response. This has been found to be particularly true for prostaglandins of the E series.

Various methods have been used in attempting to overcome this well-known inflammatory response. Stjernschantz et at. (WO 90/02553) have striven to synthesize derivatives of naturally-occurring prostaglandins in order to design out selectively the inflammatory response while maintaining the IOP-lowering effect. Others, including Ueno et at. (EP 330 511 A2) and Wheeler (EP 435 682 A2) have tried complexing prostaglandins with various cyclodextrins.

SUMMARY OF THE INVENTION

It has been unexpectedly discovered that co-administration of an E series prostaglandin and an F series prostaglandin in combination produces a greater reduction of IOP than the same dose of either type of compound given separately. In fact, as described in greater detail below, representative mixtures of the prostaglandins of the present invention produce a profound and long lasting IOP decrease. Administration of both types of prostaglandins in combination is apparently necessary to produce the desired IOP lowering effect for glaucoma therapy, while decreasing the likelihood of systemic side effects.

The extremely low dosage of the prostaglandin combinations of the present invention prevents or markedly decreases the local and/or systemic side effects seen with other glaucoma therapies—especially those based on PG therapy. A dosage of a compound of formula (I) adequate to lower IOP produces local irritation and discomfort. The combination of a compound of formula (I) and a compound of formula (II) allows this dosage to be decreased by 90% or more, thereby eliminating or substantially reducing such irritation and discomfort.

Both $PGF_{2\alpha}$ and PGE2 are naturally formed by the eye, and are normally present in aqueous humor as a combination. In addition, corneal tissue is capable of transforming exogenous $PGF_{2\alpha}$ into PGE2 such that the PGE2 concentration in aqueous humor is increased following topical ocular dosing with $PGF_{2\alpha}$. It is therefore reasonable to propose that the potent IOP lowering effect of the present PG combinations is somehow attributable to the combination of a compound of formula (I), with a compound of formula (II). The limited response to dosage with $PGF_{2\alpha}$ alone is consistent with this proposed explanation. Although the mechanism for the observed synergism is unknown, it is clear that dosage with an optimum combination of a compound of formula (I) and a compound of formula (II) will allow a more potent reduction of intraocular pressure without the side-effects produced by treatment with an adequate dose of a single component.

DETAILED DESCRIPTION OF THE INVENTION

The compounds of the present invention are known. See, for example, *The Merck Index*, 10th Edition (1983), which is incorporated herein by reference to the extent that it describes the preparation and known pharmacological profiles of $PGF_{2\alpha}$ and $PGE_2$. See also DE 2,223,365 (Bowler) and WO 90/02553 (Stjernschantz et at.).

As used in this "Detailed Description of the Invention," the term "$PGF_{2\alpha}$" shall refer to the prostaglandins of formula (I), and the term "$PGE_2$" shall refer to the prostaglandins of formula (II).

Prostaglandins of the F series which are useful in the present invention have the general formula (I), shown below:

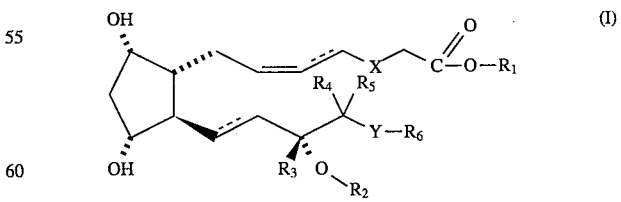

wherein:
X and Y can be the same or different, and are: $CH_2$ or O;
$R_1$ is hydrogen, a cationic salt moiety, a pharmaceutically acceptable amine moiety or a pharmaceutically acceptable ester moiety derived from the corresponding alcohol; and $R_2$ is hydrogen or a pharmaceutically acceptable ester moiety derived from the corresponding carboxylic acid.

$R_3$, $R_4$ and $R_5$ can be the same or different, and are: H or $CH_3$, with the proviso that if $R_3$ is $CH_3$, then $R_4$ and $R_5$ are H; and $R_6$ is: $C_{2-7}$ alkyl, thienyl or aryl, optionally substituted with one or more of the following: $C_{105}$ alkyl, trifluoromethyl, or a halogen;

with the proviso that if Y is O, and $R_6$ is aryl, then the aryl group must contain at least one substituent.

The following are preferred compounds of formula (I): cloprostenol, fluprostenol, PhXA41, 16,16-dimethyl-$PGF_{2\alpha}$, 15-methyl-$PGF_{2\alpha}$, 16-( 3,5-dichloro-phenoxy)-$PGF_{2\alpha}$, tiaprost, 17-phenyl-$PGF_{2\alpha}$, 17-m-chlorophenyl-$PGF_{2\alpha}$, 17-m-trifluoromethylphenyl-$PGF_{2\alpha}$, 17-(3,5-dichlorophenyl)-$PGF_{2\alpha}$, and the 3-oxa- and 13,14-dihydro-derivatives of each, as appropriate. Structures of some of the preferred compounds are shown in the following Table 1. It is most preferred to use: cloprostenol, fluprostenol and PhXA41.

TABLE 1

| COMPOUND NAME | STRUCTURE |
|---|---|
| 1) PhXA41 | 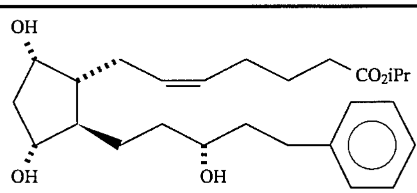 |
| 2) 16,16-dimethyl $PGF_{2\kappa}$ | 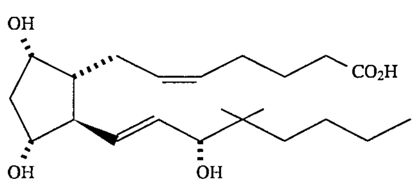 |
| 3) cloprostenol | 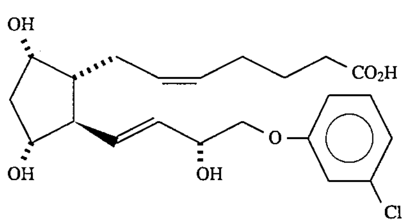 |
| 4) fluprostenol | 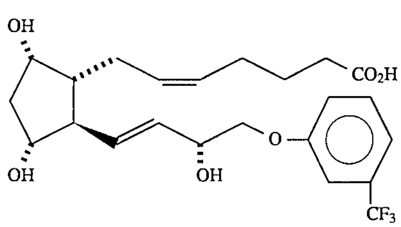 |
| 5) 13,14-dihydro-cloprostenol | 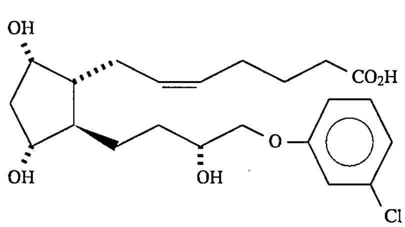 |

TABLE 1-continued

| COMPOUND NAME | STRUCTURE |
|---|---|
| 6) 3-oxa-cloprostenol | 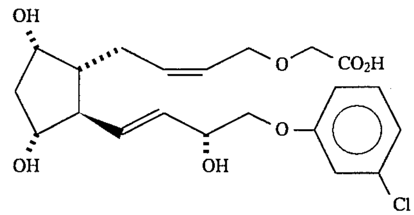 |
| 7) 15-methyl $PGF_{2\kappa}$ | 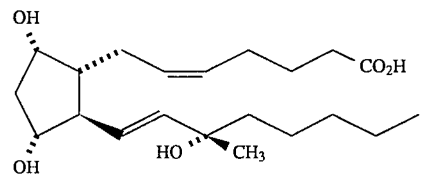 |
| 8) 15-acetyl-16,16-dimethyl-$PGF_{2\kappa}$ | 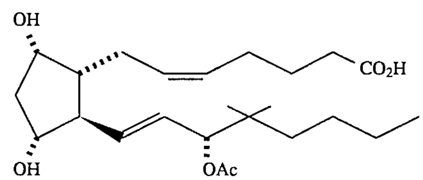 |

Prostaglandins of the E series which are useful in the present invention have the general formula (II), shown below:

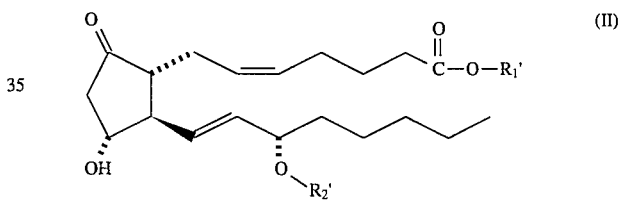

wherein:

$R'_1$ is hydrogen, a cationic salt moiety, a pharmaceutically acceptable amine moiety or a pharmaceutically acceptable ester moiety derived from the corresponding alcohol; and $R'_2$ is hydrogen or a pharmaceutically acceptable ester moiety derived from the corresponding carboxylic acid.

As used herein, the term "pharmaceutically acceptable salts and esters" means esters and salts of these compounds which have the same general pharmacological properties as the acid form from which they are derived, and which are acceptable from a toxicity viewpoint. Specifically included by this term are salts and esters of the type disclosed in U.S. Pat. No. 4,029,681 (Jun. 19, 1977) and in U.S. Pat. No. 4,288,616 (Sep. 8, 1981), the disclosures of which are hereby incorporated in the present specification by reference. Thus, the compounds covered by the above general formulae include the free acid ($R'_1$, $R_1$=H) and alcohol ($R'_2$, $R_2$=H), alkali and alkaline earth metal salts (e.g., Na, K, Ca, and Mg), ammonium and amine salts, and esters ($R'_1$, $R_1$=alkyl, or $R'_2$, $R_2$=acyl). Preferred salts are those involving alkali and alkaline earth metal cations, particularly sodium and potassium, and amine salts, especially tris(hydroxymethyl)aminomethane salts. Preferred esters are $C_1$-$C_{12}$ alkyl esters, particularly straight or branched $C_1$-$C_6$ alkyl esters, especially methyl, ethyl, isopropyl, cyclopropyl, cyclopropyl methyl, butyl, cyclobutyl, isobutyl, butyl or pentyl.

Alkali metal salts and alkaline earth metal salts of the acid form of (I) and (II) may be formed conventionally. The alcohol and/or acid or salt may be subsequently esterified with the appropriate acid and/or alcohol, e.g., a $C_1$-$C_3$ alkyl alcohol, to yield the final ester product embodiment of (I) and (II) according to known procedures.

In a similar manner, other esterifications may be effected as is known in the art employing other low alkyl, cycloalkyl, cycloalkyalkyl, aryl, or aryalkyl alcohols and/or acids such as isopropanol, cyclopropanol, cyclopropylmethanol, or phenyl or a benzyl alcohol. Since such esterification reactions are well known, they are not further described here.

Prostaglandins of formula (I) and formula (II) are combined in a molar ratio in the range of 0.1:1.0 to 1000:1, respectively. The preferred range is 4:1 to 20:1. Most preferred is a molar ratio of about 10:1.

The combinations of compounds of formulae (I) and (II) are useful in lowering intraocular pressure and thus are useful in the treatment of glaucoma. As compared with therapeutically effective dosages of the individual components, the combinations produce significantly fewer unwanted side effects such as marked vasoconstriction or vasodilation of the vessels of the sclera, painful stinging and intraocular inflammation.

The combinations are preferably administered topically. The dosage range for a compound of formula (I) is generally between about 0.01 and about 1000 micrograms per eye (μg/eye) and is preferably between about 0.05 and 5.0/μg/eye. The dosage range for a compound of formula (II) is generally between about 0.001 and about 5.0 μg/eye and is preferably between about 0.01 and 0.5 μg/eye. The combinations of the present invention can be administered as solutions, suspensions, or emulsions (dispersions) in a suitable ophthalmic vehicle.

In forming compositions for topical administration, the mixtures are generally formulated as between about 0.0001 to about 1.0 percent by weight (wt. %) solutions in water at a pH between 4.5 to 8.0 (figures relate to combined presence of (I) and (II)). The mixtures are preferably formulated as between about 0.0001 to about 0.1 wt. % and, most preferably, about 0.002 wt. %. While the precise regimen is left to the discretion of the clinician, it is recommended that the resulting solution be topically applied by placing one drop in each eye two times a day.

Other ingredients which may be desirable to use in the ophthalmic preparations of the present invention include preservatives, co-solvents and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level of from 0.001% to 1.0% by weight.

Co-Solvents

Prostaglandins, and particularly ester derivatives, typically have limited solubility in water and therefore may require a surfactant or other appropriate cosolvent in the composition. Such co-solvents include: Polysorbate 20, 60 and 80; Pluronic F-68, F-84 and P-103; cyclodextrin; or other agents known to those skilled in the art. Such co-solvents are typically employed at a level of from 0.01% to 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The following examples are representative pharmaceutical compositions of the invention for topical use in lowering of intraocular pressure. The Compound numbers used in the following Examples refer to the compounds of formula (I) which are listed in Table 1, above.

EXAMPLE A

| INGREDIENT | PERCENTAGE BY WEIGHT |
| --- | --- |
| (II): $R'_1 = CH_3$; $R'_2 = H$ | 0.001 |
| (I): Compound 1 | 0.02 |
| Benzalkonium chloride | 0.01 |
| Polysorbate 80 | 0.05 |
| Sodium acetate | 0.07 |
| Sodium chloride | 0.6 |
| Hydroxypropyl methyl cellulose | 0.5 |
| HCl and/or NaOH | to adjust pH |
| Purified water | q.s. to 100% |

EXAMPLE B

| INGREDIENT | PERCENTAGE BY WEIGHT |
| --- | --- |
| (II): $R'_1 = CH_3$; $R'_2 = H$ | 0.0005 |
| (I): Compound 2, methyl ester | 0.005 |
| Benzalkonium chloride | 0.01 |
| Pluronic P-84 | 0.5 |
| Dried sodium phosphate | 0.01 |
| Sodium biphosphate | 0.07 |
| Sodium chloride | 0.18 |
| HCl and/or NaOH | to adjust pH |
| Purified water | q.s. to 100% |

EXAMPLE C

| INGREDIENT | PERCENTAGE BY WEIGHT |
| --- | --- |
| (II): $R'_1 = CH_3$; $R'_2 = H$ | 0.0002 |
| (I): Compound 3, isopropyl ester | 0.001 |
| Chlorobutanol | 0.5 |
| Sodium acetate | 0.14 |
| Disodium edetate | 0.01 |
| Sodium chloride | 0.52 |
| HCl and/or NaOH | to adjust pH |
| Polyvinyl alcohol | 1.0 |
| Purified water | q.s. to 100% |

EXAMPLE D

| INGREDIENT | PERCENTAGE BY WEIGHT |
| --- | --- |
| (II): $R'_1 = CH_3$; $R'_2 = H$ | 0.0002 |
| (I): Compound 3, methyl ester | 0.002 |

-continued

| INGREDIENT | PERCENTAGE BY WEIGHT |
|---|---|
| Benzalkonium chloride | 0.01 |
| Dextran 70 | 0.1 |
| Disodium edetate | 0.05 |
| Potassium chloride | 0.12 |
| Sodium chloride | 0.77 |
| Hydroxypropyl methyl cellulose | 0.3 |
| HCl and/or NaOH | adjust pH |
| Purified water | q.s. to 100% |

EXAMPLE E

| INGREDIENT | PERCENTAGE BY WEIGHT |
|---|---|
| (II): $R'_1 = CH_3$; $R'_2 = H$ | 0.0001 |
| (I): Compound 4, isopropyl ester | 0.001 |
| Benzalkonium chloride | 0.01 |
| Dextran 70 | 0.1 |
| Disodium edetate | 0.05 |
| Potassium chloride | 0.12 |
| Sodium chloride | 0.77 |
| Hydroxypropyl methyl cellulose | 0.3 |
| HCl and/or NaOH | to adjust pH |
| Purified water | q.s. to 100% |

EXAMPLE F

| INGREDIENT | PERCENTAGE BY WEIGHT |
|---|---|
| (II): $R'_1$ = isobutyl; $R'_2 = H$ | 0.0001 |
| (I): Compound 6, ethyl ester | 0.0005 |
| Benzalkonium chloride | 0.01 |
| Dextran 70 | 0.1 |
| Disodium edetate | 0.05 |
| Potassium chloride | 0.12 |
| Sodium chloride | 0.77 |
| Hydroxypropyl methyl cellulose | 0.3 |
| HCl and/or NaOH | to adjust pH |
| Purified water | q.s. to 100% |

EXAMPLE G

| INGREDIENT | PERCENTAGE BY WEIGHT |
|---|---|
| (II): $R'_1 = CH_2CH_3$; $R'_2 = H$ | 0.0002 |
| (I): Compound 7, isopropyl ester | 0.001 |
| Benzalkonium chloride | 0.01 |
| Dextran 70 | 0.1 |
| Disodium edetate | 0.05 |
| Potassium chloride | 0.12 |
| Sodium chloride | 0.77 |
| Hydroxypropyl methyl cellulose | 0.3 |
| HCl and/or NaOH | adjust pH |
| Purified water | q.s. to 100% |

EXAMPLE H

| INGREDIENT | PERCENTAGE BY WEIGHT |
|---|---|
| (II): $R'_1 = CH_3$; $R'_2 = H$ | 0.0001 |
| (I): Compound 8, ethyl ester | 0.005 |
| Benzalkonium chloride | 0.01 |
| Dextran 70 | 0.1 |
| Disodium edetate | 0.05 |
| Potassium chloride | 0.12 |
| Sodium chloride | 0.77 |
| Hydroxypropyl methyl cellulose | 0.3 |
| HCl and/or NaOH | to adjust pH |
| Purified water | q.s. to 100% |

EXAMPLE J

| INGREDIENT | PERCENTAGE BY WEIGHT |
|---|---|
| (II): $R'_1 = CH_3$; $R'_2 = H$ | 0.001 |
| (I): Compound 5, isopropyl ester | 0.004 |
| Benzalkonium chloride | 0.02 |
| Polysorbate 80 | 0.15 |
| Dibasic sodium phosphate | 0.15 |
| Monobasic sodium phosphate | 0.05 |
| Sodium chloride | 0.75 |
| Disodium EDTA | 0.01 |
| HCl and/or NaOH | to adjust pH |
| Purified water | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A topical ophthalmic composition for the treatment of glaucoma and ocular hypertension, said composition comprising an ophthalmically acceptable carrier and a therapeutically effective amount of a combination of:

a) a non-inflammatory amount of a compound of formula (I):

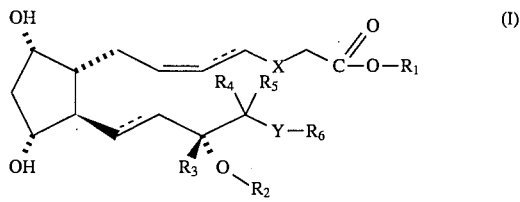

wherein:
X and Y can be the same or different, and are: $CH_2$ or O;
$R_1$ is hydrogen, a cationic salt moiety, a pharmaceutically acceptable amine moiety or a pharmaceutically acceptable ester moiety derived from the corresponding alcohol; and
$R_2$ is hydrogen or a pharmaceutically acceptable ester moiety derived from the corresponding carboxylic acid.
$R_3$, $R_4$ and $R_5$ can be the same or different, and are: H or $CH_3$, with the proviso that if $R_3$ is $CH_3$, then $R_4$ and $R_5$ are H; and
$R_6$ is: $C_{2-7}$ alkyl, thienyl or aryl, optionally substituted with one or more of the following: $C_{1-5}$ alkyl, trifluoromethyl, or a halogen;

with the proviso that if Y is O, and $R_6$ is aryl, then the aryl group must contain at least one substituent; and b) a non-inflammatory amount of a compound of formula (II):

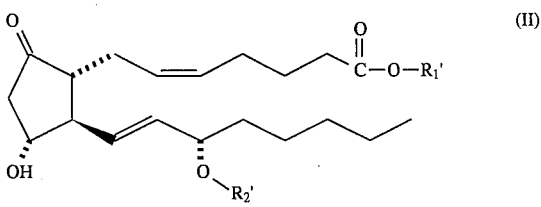

wherein:

$R'_1$ is hydrogen, a cationic salt moiety, a pharmaceutically acceptable amine moiety or a pharmaceutically acceptable ester moiety derived from the corresponding alcohol; and $R'_2$ is hydrogen or a pharmaceutically acceptable ester moiety derived from the corresponding carboxylic acid; and wherein the molar ratio of (I):(II) is at least about 0.1:1.

2. The composition of claim 11, wherein the compound of formula (I) is selected from the group consisting of: cloprostenol, fluprostenol, PhXA41, 16,16-dimethyl-$PGF_{2\alpha}$, 15-methyl-$PGF_{2\alpha}$, 16-(3,5-dichloro-phenoxy)-$PGF_{2\alpha}$, tiaprost, 17-phenyl-$PGF_{2\alpha}$, 17-m-chlorophenyl-$PGF_{2\alpha}$, 17-m-trifluoromethylphenyl-$PGF_{2\alpha}$, 17-(3,5-dichlorophenyl)-$PGF_{2\alpha}$, and the 3-oxa- and 13,14-dihydro- derivatives thereof.

3. The composition of claim 2, wherein the compound of formula (I) is selected from the group consisting of: cloprostenol, fluprostenol and PhXA41.

4. The composition of claim 1, wherein the molar ratio of (I):(II) is less than about 1000:1.

5. The composition of claim 4, wherein the molar ratio of (I):(II) is between about 4:1 and about 20:1.

6. The composition of claim 4, wherein the molar ratio of (I):(II) is about 10:1.

7. The composition of claim 1, wherein the concentration of the combination of a compound of formula (I) and a compound of formula (II) is between about 0.0001 and about 1.0 percent by weight/volume.

8. The composition of claim 7, wherein the concentration of the combination of a compound of formula (I) and a compound of formula (II) is between about 0.0001 and about 0.1 percent by weight/volume.

9. The composition of claim 8, wherein the concentration of the combination of a compound of formula (I) and a compound of formula (II) is about 0.002 percent by weight/volume.

10. A method of treating glaucoma and ocular hypertension which comprises topically administering to the affected eye a therapeutically effective amount of a composition comprising an ophthalmically acceptable carrier and a combination of:

a) a non-inflammatory amount of a compound (I) selected from the group consisting of: cloprostenol, fluprostenol, PhXA41, 16,16-dimethyl-$PGF_2$, 15-methyl-$PGF_2$, 16-(3,5-dichloro-phenoxy)-$PGF_2$, tiaprost, 17-phenyl-$PGF_2$, 17-m-chlorophenyl-$PGF_2$, 17-m-trifluoromethylphenyl-$PGF_2$, 17-(3,5-dichlorophenyl)-$PGF_2$, and the 3-oxa- and 13,14-dihydro-derivatives thereof; and b) a non-inflammatory amount of compound of formula (II):

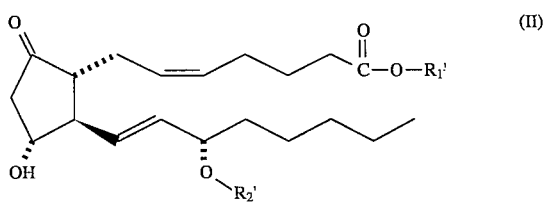

wherein:

$R_1$ is hydrogen, cationic salt moiety, a pharmaceutically acceptable amine moiety derived from the corresponding alcohol; and $R_2$ is hydrogen or a pharmaceutically acceptable ester moiety derived from the corresponding carboxylic acid; and wherein the molar ratio of (I):(II) is at least about 0.1:1.

11. The method of claim 2, wherein the compound (I) is selected from the group consisting of: cloprostenol, fluprostenol and PhXA41.

12. The method of claim 2, wherein about 0.01 and about 1000 micrograms of the compound (I) is administered.

13. The method of claim 7, wherein between about 0.05 and about 5.0 micrograms of the compound (I) is administered.

14. The method of claim 2, wherein between about 0.001 and about 5.0 micrograms of the compound (I) is administered.

15. The method of claim 14, wherein between about 0.01 and about 0.05 micrograms of the compound (I) is administered.

16. The method of claim 2, wherein the molar ratio of (I):(II) is less than about 1000:1.

17. The method of claim 16, wherein the molar ratio of (I):(II) is between about 4:1 and about 20:1.

18. The method of claim 17, wherein the molar ratio of (I):(II) is about 10:1.

* * * * *

UNITED STATES PATENT AND TRADEMARK OFFICE
CERTIFICATE OF CORRECTION

PATENT NO. : 5,565,492
DATED : Oct. 15, 1996
INVENTOR(S) : Louis M. DeSantis and Verney L. Sallee It is certified that error appears in the above-indentified patent and that said Letters Patent is hereby corrected as shown below:

<u>Column 1</u>: In the structure at line 31, replace triple bond with double bond.
In the structure at line 40, replace triple bond with double bond.

<u>Column 3</u>: Line 7, change "$C_{105}$" to --$C_{1-5}$--.

<u>Column 9</u>: Claim 1, in the structure at line 8, change "$R_1'''$" to --$R'_1$--.
Claim 1, in the structure at line 12, change "$R_2'''$" to --$R'_2$--.
Claim 2, line 22, change "11" to --1--.

UNITED STATES PATENT AND TRADEMARK OFFICE
CERTIFICATE OF CORRECTION

PATENT NO. : 5,565,492
DATED : Oct. 15, 1996
INVENTOR(S) : Louis M. DeSantis and Verney L. Sallee It is certified that error appears in the above-indentified patent and that said Letters Patent is hereby corrected as shown below:

Column 10: Claim 10, in the structure at line 17, change "$R_1'''$" to --$R'_1$--.
Claim 10, in the structure at line 21, change "$R_2'''$" to --$R'_2$--.
Claim 10, line 24, change "$R_1$" to -- $R'_1$--.
Claim 10, line 27, change "$R_2$" to -- $R'_2$--.
Claim 11, line 31, change "claim 2" to --claim 10--.
Claim 12, line 34, change "claim 2" to --claim 10--.
Claim 12, line 34, after "wherein" insert --between--.
Claim 13, line 36, change "claim 7" to --claim 12--.
Claim 14, line 40, change "claim 2" to --claim 10--.
Claim 14, line 41, change "I" to --II--.
Claim 15, line 44, change "I" to --II--.
Claim 16, line 46, change "claim 2" to --claim 10--.

Signed and Sealed this

Twenty-ninth Day of April, 1997

Attest:

BRUCE LEHMAN

*Attesting Officer*  *Commissioner of Patents and Trademarks*